United States Patent [19]

Holzgang et al.

[11] Patent Number: 4,536,755

[45] Date of Patent: Aug. 20, 1985

[54] APPARATUS FOR DETECTING UNAUTHORIZED EGRESS BY PATIENT FROM POSITION OF CONFINEMENT

[75] Inventors: Curtis R. Holzgang, Beaverton; Mark K. Leavitt, Portland; Alfred D. Doney, Oregon City; James Kuehn, Gladstone, all of Oreg.

[73] Assignee: Rigi Systems, Inc., Beaverton, Oreg.

[21] Appl. No.: 473,000

[22] Filed: Mar. 7, 1983

[51] Int. Cl.³ ............................................. G08B 21/00
[52] U.S. Cl. .................................. 340/573; 340/689; 200/61.52; 200/DIG. 2
[58] Field of Search ............... 340/573, 689, 686, 530; 200/DIG. 2, 61.52, 61.47

[56] References Cited

U.S. PATENT DOCUMENTS

| | | | |
|---|---|---|---|
| 299,649 | 6/1884 | Keep et al. | 340/573 |
| 2,260,715 | 10/1941 | Ketchum | 340/573 |
| 2,425,790 | 8/1947 | Fletcher | 340/573 |
| 3,325,799 | 6/1967 | Farris | 340/573 |
| 3,547,106 | 12/1970 | Bornmann | 340/573 |
| 3,781,843 | 12/1973 | Harrison et al. | 340/573 |
| 3,796,208 | 3/1974 | Bloice | 340/573 |
| 3,961,201 | 6/1976 | Rosenthal | 340/573 |
| 3,991,414 | 11/1976 | Moran | 340/573 |
| 4,020,482 | 4/1977 | Feldl | 340/573 |
| 4,067,005 | 1/1978 | Levy et al. | 340/573 |
| 4,175,263 | 11/1979 | Triplett et al. | 340/573 |
| 4,196,425 | 4/1980 | Williams, Jr. et al. | 340/573 |
| 4,263,586 | 4/1981 | Nicholas | 340/573 |
| 4,348,562 | 9/1982 | Florin | 200/61.52 |

Primary Examiner—Glen R. Swann, III
Attorney, Agent, or Firm—Klarquist, Sparkman, Campbell, Leigh & Whinston

[57] ABSTRACT

An apparatus and a method for monitoring the activity of a patient comprehend the sensing of the downwardly directed angular inclination of the distal end of the patient's femur to determine when the patient is in an ambulatory enabling position. The electrodes of a mercury switch, which is included in an alarm module that is attached to the patient's thigh, close to produce an electric signal whenever such inclination exceeds a preselected threshold angle. Such signal activates an alarm-generating electrical circuit to produce an alarm with a distinctive sound to provide notice to attending personnel of the possibility of impending injury to the patient.

5 Claims, 7 Drawing Figures

APPARATUS FOR DETECTING UNAUTHORIZED EGRESS BY PATIENT FROM POSITION OF CONFINEMENT

BACKGROUND OF THE INVENTION

The present invention relates to apparatus and methods for monitoring patient activity, and in particular, to an apparatus and a method which provides notice to attending personnel of the possibility of impending injury to the patient.

Systems have been known heretofore for monitoring the activity of a patient for whom there is a substantial likelihood of injury if the patient is permitted to ambulate without assistance.

One type of such system, as exemplied by U.S. Pat. No. 3,781,843 of Harrison, et al., makes use of fluid-filled sensors attached to the top portions of the side rails and footboard of a bed. An alarm is triggered in response to the displacement of a predetermined volume of fluid which is caused by the patient's grasping the sensors as he attempts to leave the bed. This system suffers from the disadvantage of operational failure and inconvenience due to fluid leaks in the sensors. In addition, such a system would be difficult to adapt for use on the arm rests of a wheelchair to which a patient may be confined.

Another type of system makes use of pneumatic pressure sensors to monitor patient activity. U.S. Pat. No. 4,020,482 of Feldl describes a patient monitor which comprises an elongated air-inflated flexible bag which is placed between the mattress and springs of a bed. The air-inflated bag is operatively connected to a pressure-actuated electrical switch which closes to produce a signal that activates an alarm whenever the weight of the patient is removed, thereby to indicate that the patient is attempting to leave the bed.

U.S. Pat. No. 4,175,263 of Triplett, et al. describes a patient monitor which makes use of two pneumatically inflated pressure sensors. One sensor measures the weight of the patient while he is lying in bed, and the other sensor measures the pressure applied to the guard rails of the bed by the arms of the patient when he is attempting to leave the bed. An alarm is activated in response to the detection of a shift in weight from the first pressure sensor to the second pressure sensor to indicate that the patient is attempting to leave the bed.

The systems described by Feldl and Triplett, et al. suffer from the disadvantage of operational failure due to a reduction in air pressure or air leaks in the sensors. In addition, such systems are not readily adaptable for use in monitoring the activity of a patient confined to a wheelchair or other patient transportation means.

A third type of system, as exemplified by U.S. Pat. No. 3,547,106 of Bornmann, employs an activity detecting system which makes use of a magnet secured to the patient and positioned proximate to a stationary sensing coil to produce an electric signal in response to the changing magnetic field caused by the relative movement between the magnet and the sensing coil. Such a system is reported to be potentially useful for monitoring cyclic movement, such as that produced by the patient's breathing, but would appear to be too sensitive to be responsive only to patient ambulatory movement.

A fourth type of system, as exemplied by U.S. Pat. No. 3,796,208 of Bloice and U.S. Pat. No. 4,196,425 of Williams, Jr., et al., utilizes an electromagnetic wave energy source to produce a field surrounding at least a part of the patient and a detector to measure the disturbance of the electric field caused by movement of the patient. As in the case of the magnetic field sensing system, an elaborate system of this type would appear to be too sensitive to distinguish the attempt of a patient to leave an area of confinement from movement due to normal breathing or mere restlessness of the patient.

The fifth and most common type of patient activity monitoring system makes use of pressure sensitive electric switches which are responsive to the weight of the patient to indicate whether the patient has remained in bed. For example, U.S. Pat. No. 4,263,586 of Nicholas and U.S. Pat. No. 2,425,790 of Fletcher disclose the use of a pressure-operated electric switch which is installed under a leg of a bed to produce a signal in response to the lessening of the weight on the leg when the patient leaves the bed.

U.S. Pat. No. 3,325,799 of Farris and U.S. Pat. No. 2,260,715 of Ketchem describe the use of a pressure-operated electric switch which is installed beneath or within the mattress of the bed.

U.S. Pat. No. 4,067,005 of Levy, et al.; U.S. Pat. No. 3,961,201 of Rosenthal; and U.S. Pat. No. 299,649 of Keep, et al. exemplify the use of electric switches connected to the side rails, headboard, and footboard of the bed to detect the movement of a patient attempting to climb over them.

U.S. Pat. No. 3,991,414 of Moran discloses the use of a mercury switch housed in a cartridge which is mounted on a portion of a bed frame for pivotal movement in response to the deflection of two deflection elements which move in accordance with the shift in weight of a patient who is changing positions on or is departing from the bed. A patient leaving the bed removes his weight therefrom to permit pivotal movement of the mercury switch. Such pivotal movement alters the position of the mercury contained within the switch cartridge so that the mercury comes into contact with the two spaced-apart switch electrodes to close the switch and produce an electric signal indicating that the patient has left the bed.

All of the aforementioned activity monitors of this type suffer from the disadvantage of being permanently attached to the bed and, therefore, are not readily adaptable for use with a wheelchair or other transportation device to which a patient could be confined. The systems are also susceptible to the giving of false alarms, thereby to be unreliable, possibly even creating a nuisance for attending personnel.

An object of this invention, therefore, is to provide an apparatus and a method which produces a definitive indication that a patient has assumed an ambulatory enabling position and thereby may be in imminent danger of injury.

Another object of this invention is to provide such an apparatus and a method which comprehend the sensing of the downwardly directed inclination of the distal end of the femur portion of the patient's leg to indicate that the patient is in an enabling position or is attempting to leave the bed, chair, or gurney he has been occupying.

A further object of this invention is to provide such an apparatus which is portable and is worn by the patient to facilitate continuous monitoring of the patient's activity.

Still another object of this invention is to provide such an apparatus which produces an alarm signal that is indicative of impending patient egress from one of the various types of objects which he might occupy.

SUMMARY OF THE INVENTION

This invention overcomes the deficiencies noted in the systems described hereinabove by providing an apparatus and a method for monitoring patient activity which provide a warning that the patient may be attempting to leave the bed or chair he has been occupying.

The apparatus of the present invention comprises an angle inclination sensing means which senses angular displacement relative to a predetermined datum plane. The sensing means is secured to and positioned on the femur portion of a patient's leg to be responsive to the downwardly directed angular inclination of the distal end thereof. A threshold detecting means is operatively connected to the sensing means and produces a signal whenever the distal end of the femur portion of the patient's leg assumes a downwardly directed angular inclination exceeding a preselected amount. A warning means in communication with the detecting means is actuated in response to the signal to provide notice to attending personnel that the patient is in an ambulatory enabling position and may be in danger of imminent injury.

The method of the present invention comprises the steps of determining that the downwardly directed angular inclination of the distal end of the femur portion of the patient's leg has exceeded a preselected amount and providing notice that the inclination of the distal end of the femur has exceeded the preselected amount to indicate that the patient is in an ambulatory enabling position.

A preferred embodiment of the apparatus of the invention includes a portable alarm module which is attached to and positioned on the femur portion of the leg by means of an elastic band. Included within the alarm module is a mercury switch which contains a small quantity of mercury that changes position within the switch container in accordance with the angular disposition of the switch. Actuation of the mercury switch is accomplished by orienting the switch in a downwardly directed position to allow the mercury to flow to the end of the switch housing where two spaced-apart electrodes are embedded. Contact of the mercury with the two electrodes forms a conduction path between the two electrodes to close the switch and produce an electric signal which activates an audible alarm.

The apparatus senses the downwardly directed angular disposition of the portion of the femur proximal the knee as a means to establish definitively that the patient is in an enabling position to leave his object of confinement, be it a bed or chair. The mercury switch is oriented on the patient's leg for actuation in response to an amount of gravitational force which corresponds to a preselected amount of downwardly directed inclination of the distal end of the patient's femur. For example, whenever a patient is in bed, the angle corresponding to the extent of downwardly directed incline of the distal end of the femur portion of the leg from a horizontal position will exceed the preselected threshold (generally approximately 60°) only when the patient assumes an enabling position to leave the bed, e.g., by either kneeling or standing. Thus, a mercury switch positioned on the leg to measure a threshold angle in excess of 60° will not be actuated by any movements of the patient other than an attempt to assume a kneeling position on the bed.

An angle inclination sensing means of the type described which is positioned on the femur proximal the knee, therefore, is insensitive to the angular position of the knee whenever the patient is lying in the prone or supine positions, sitting in a chair, or assuming any position other than those preparatory to kneeling or standing. The invention takes advantage of the inherent property of the distal end of the femur as an unambiguous indicator of patient movement that can result in potential injury to the patient.

The preferred embodiment of the apparatus of the present invention is worn by the patient, and thereby provides a portable system for monitoring patient movements in preparation to leave hospital transportation devices, such as a wheelchair. In the case of the wheelchair, the mercury switch will be actuated whenever the patient attempts to leave the seat.

Whenever the threshold angle of the mercury switch is exceeded, a local or remote warning signal can be produced to alert attending personnel to the possibility of impending patient injury.

The apparatus of the invention also includes means to provide a time delay between actuation of the angle inclination sensing means and actuation of the alarm means to avert false alarms caused by momentary actuation of the switch due to patient movement between nonhazardous positions.

In addition, the apparatus includes a pressure-sensitive switch to provide a means to detect the unauthorized removal of the monitoring system. The pressure-sensitive switch is actuated in response to a substantial change in contact pressure between the patient's leg and the alarm module.

The foregoing and other objects, features, and advantages of the present invention will become more apparent from the following detailed description of a preferred embodiment which proceeds with reference to the accompanying drawings.

DETAILED DESCRIPTION OF PREFERRED EMBODIMENT

General Description of Monitoring System Assembly

Figure 1:
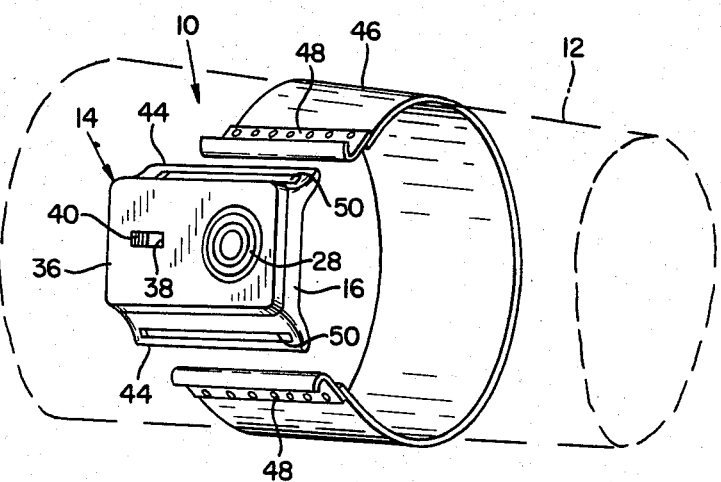
FIG. 1 is a frontal exploded isometric view of the apparatus of the present invention showing the alarm module in conjunction with an elastic band adapted to encompass a patient's thigh, which is depicted in phantom.
Figure 2:
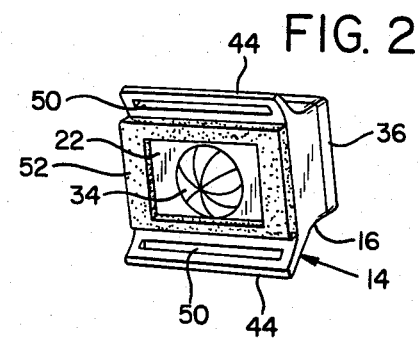
FIG. 2 is a rear isometric view showing the membrane-sealed pressure switch for detecting unauthorized removal of the apparatus of FIG. 1.
Figure 3:
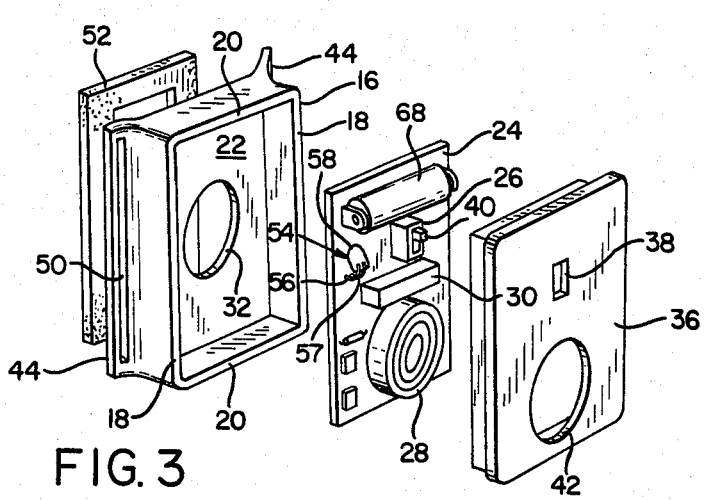
FIG. 3 is an exploded view of the alarm module of FIGS. 1 and 2.

With reference to FIGS. 1-3, the apparatus of the present invention comprises monitoring system 10 which is positioned on the anterior surface of the patient's thigh 12. Monitoring system 10 comprises alarm module 14 which includes a substantially rectangular carrier portion 16 having elongated side walls 18 and top and bottom walls 20 perpendicularly disposed to the surface of rear wall 22 to form an open ended, shallow container to receive circuit board 24. Circuit board 24 carries all of the electrical components which sense the angular inclination of the distal end of the patient's femur and produce an alarm signal as will be further hereinafter described.

ON-OFF switch 26 and audio transducer 28 project from the upper surface of circuit board 24 where the circuit components are installed. The contacts of pressure switch 30 project from the lower surface of circuit board 24 and extend through circular aperture 32 of rear wall 22 of the carrier to engage the anterior surface of the patient's thigh for the purpose of detecting the unauthorized removal of the monitoring system. Membrane 34 provides a moisture barrier seal to protect the electrical circuit from corrosion and damage.

Face plate 36 covers the open end of carrier 16 to enclose alarm module 14. Rectangular aperture 38 is included in face plate 36 to provide access to the slidable actuating member 40 of the ON-OFF switch 26. The top surface of actuating member 40 is mounted flush with the surface of face plate 36 so that ON-OFF switch 26 can be actuated only with the use of a scribe or other pointed instrument. This enhances the probability that the alarm will be disarmed only by authorized personnel. Circular aperture 42 is included in face plate 36 to provide clearance for the cylindrically shaped audio transducer 28 which projects therethrough.

The overall assembly of alarm module 14 preferably should withstand contact with water and chemicals used during a sterilizing wipe-down procedure on the patient's leg.

Parallel to side walls 18 of carrier 16 are two outwardly and rearwardly extending flange portions 44 which provide conformal coverage of alarm module 14 over the anterior surface of the thigh. Monitoring system 10 is secured to the patient's thigh by means of a detachable, sterilizable elastic band 46 which circumferentially encompasses the thigh. Each end of elastic band 46 terminates in an elongated, arcuate clasp 48 which is received by the elongated slot 50 included within each flange 44 for attachment to alarm module 14 at the anterolateral and anteromedial portions of the thigh.

To secure monitoring system 10 in place and enhance patient comfort, precut adhesive-backed foam pad 52 is attached to rear wall 22 of carrier 16 to serve as an interface between the patient's thigh and alarm module 14.

Angle Inclination Sensor and Threshold Detector

Figure 4:
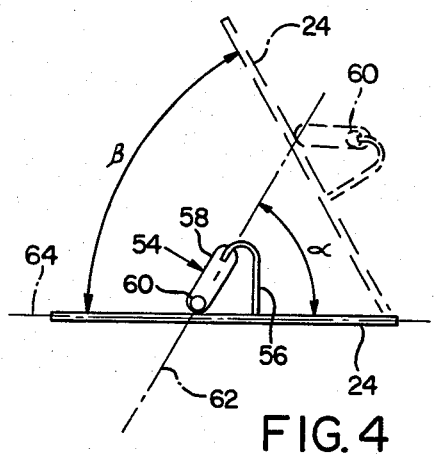
FIG. 4 is a diagram showing the placement of the mercury switch on the circuit board to set the inclination threshold angle.

With reference to FIGS. 3 and 4, mercury switch 54, such as the Model No. 411 manufactured by Ray-May & Associates of Garland, Tex. is shown mounted to circuit board 24 by means of switch electrodes 56 and 57 which extend from one end of the switch housing 58 and are soldered to metallized areas on the circuit board. Mercury switch 54 constitutes an angle inclination sensing means to sense angular displacement relative to a reference datum plane. Sensing of the downwardly directed angular inclination of the distal end of the patient's femur is accomplished by orienting mercury switch 54 on circuit board 24 so that whenever the monitoring system is secured to the patient's thigh, an upwardly or downwardly directed angular inclination of the femur portion of the leg proximal the knee has the effect of adjusting the position of the mercury 60 contained within switch housing 58. A downwardly directed inclination of the leg will bring the mercury into contact with the portions of electrodes 56 and 57 extending inside switch housing 58 whenever a preselected inclination threshold angle is exceeded. Contact by the mercury 60 with electrodes 56 and 57 forms a conduction path between the two electrodes, thereby effecting closure of the mercury switch to produce an electric signal as will be further hereinafter described.

With particular reference to FIG. 4, the inclination threshold angle for actuating mercury switch 54 is set by the inclined mounting of switch housing 58 to circuit board 24. The angle $\alpha$ formed between central longitudinal axis 62 of switch housing 58 and the surface of circuit board 24 is fixed at approximately the preselected threshold amount of the downwardly directed angular inclination of the distal end of the femur.

Figure 5:
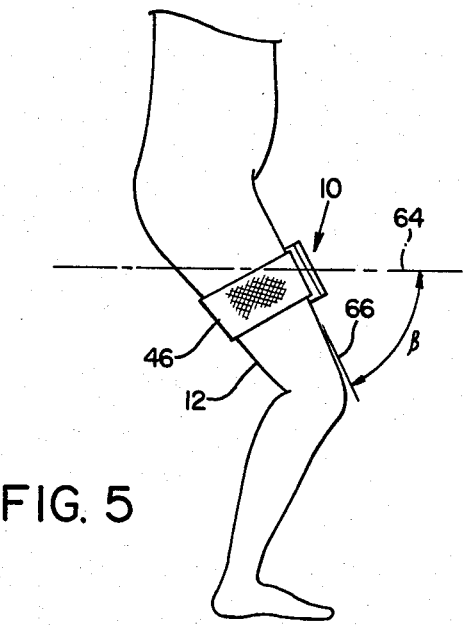
FIG. 5 is a diagram showing the monitoring system worn by a patient whose leg is inclined at the preferred threshold angle which actuates the alarm signal.

With particular reference to FIG. 5, such inclination of the femur is represented as angle $\beta$, which is measured between horizontal plane 64 and datum line 66 representing the slope of the anterior surface of the patient's thigh. Thus, if the slight inclination of the anterior surface of the thigh is neglected, angle $\alpha$ is equal to angle $\beta$. A value of $\beta$ equal to 60° is deemed adequate to distinguish movements characteristic of an overactive or restless patient from those of a patient who may be attempting to leave the object he has been occupying. Mercury switch housing 58 is secured in position on the circuit board by epoxy glue, potting material, or any other suitable bonding material.

Alarm Signal Generator

Figure 6:
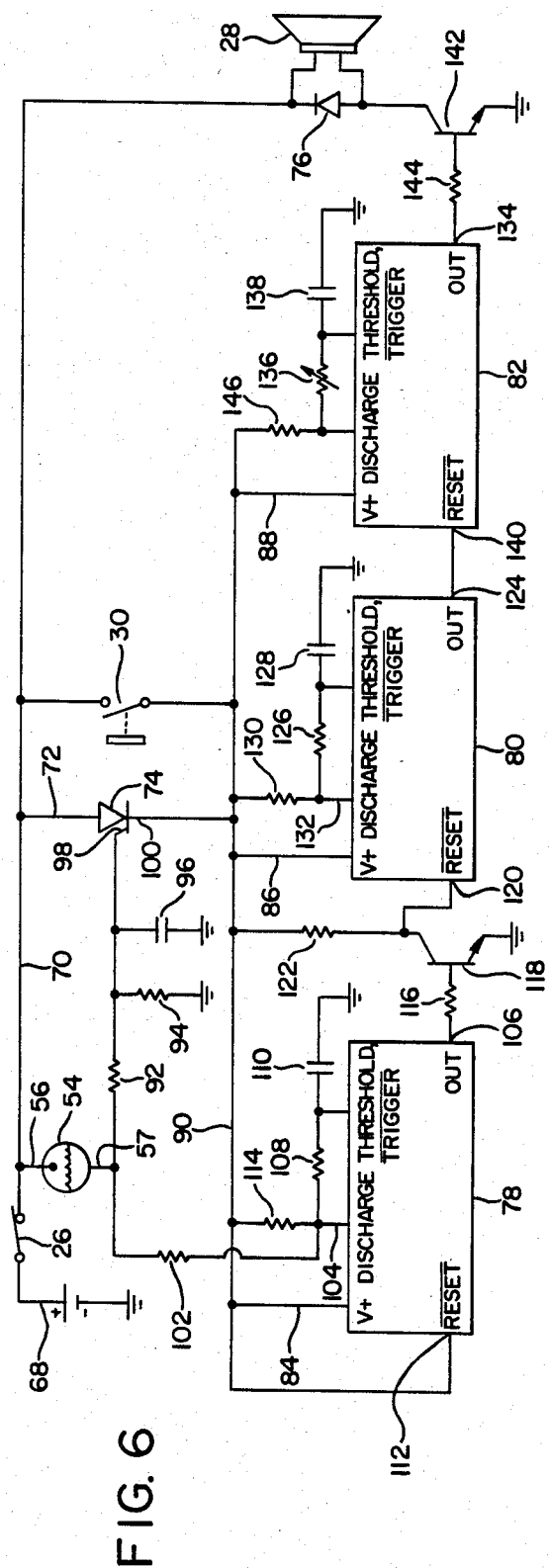
FIG. 6 is an electrical circuit diagram of the alarm signal generator of FIGS. 1-3.
Figure 7:
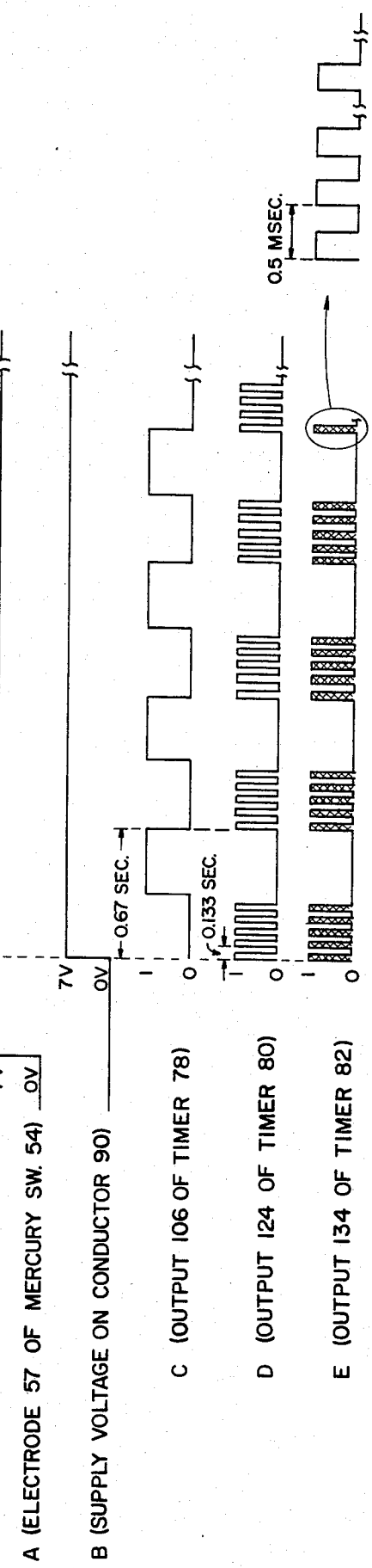
FIG. 7 is a logic timing diagram associated with the alarm signal generating circuit of FIG. 6.

With reference to FIGS. 6 and 7, an alarm signal generating electrical circuit comprises a warning means that produces an audible alarm signal whenever the angular inclination of the distal end of the patient's femur has exceeded the preselected threshold amount, thereby indicating that the patient is in an ambulatory enabling position.

The electrical circuit includes a seven volt battery 68, such as a model TR 175T mercury battery manufactured by Duracell Inc., which is applied to ON-OFF switch 26 to provide a switchable source of DC power to the remaining portions of the alarm circuit through electrical conductor 70. Whenever switch 26 is closed, and thereby is set to the ON position, the battery voltage is applied to electrode 56 of mercury switch 54, anode 72 of SCR 74, pressure switch 30, and the junction of the cathode of diode 76 and one of the input leads to audio transducer 28. Under normal operating conditions, however, the circuit remains de-energized and no electric current is drawn from battery 68. Such a condition is satisfied as long as pressure switch 30 remains open, which indicates that alarm module 14 remains properly in place on the patient's thigh, and mercury switch 54 remains nonconducting, which indicates that the downwardly directed inclination of the patient's femur has not exceeded the preselected threshold amount. Under these conditions, no electric current flows through audio transducer 28 to sound an alarm.

An audible alarm signal is synthesized by three integrated circuit timers 78, 80, and 82, all of which operate in the astable mode and are electrically interconnected to produce pulse triggered oscillations that provide an alarm signal with a distinctive sound. Timing devices suitable for such an application are, for example, the ICM 7555/7556 CMOS general purpose timers manufactured by Intersil. Each timer 78, 80, and 82 has a corresponding supply voltage terminal 84, 86, and 88, all of which are interconnected to electrical conductor 90. SCR 74 provides the supply voltage to electrical conductor 90, which voltage is applied by battery 68, to activate the alarm upon the patient's movement to an ambulatory enabling position. Pressure switch 30 provides the supply voltage to activate the alarm upon unauthorized removal of the monitoring system.

Whenever ON-OFF switch 26 is set in the ON position and mercury switch 54 is actuated, the voltage of battery 68 is immediately applied to a time delay generating subcircuit comprising resistors 92 and 94 and capacitor 96. The output of the time delay circuit is interconnected direct to gate electrode 98 of SCR 74. SCR 74 will conduct electric current from its anode 72 to its cathode 100 whenever the DC voltage that is developed across capacitor 96 and is applied to gate 98 is of sufficient magnitude. An operational characteristic of the SCR is that once having been triggered by the gate signal, the device will maintain current flow from the anode to the cathode irrespective of the gate voltage or gate current. Thus, SCR 74 will conduct electric current, and thereby apply the supply voltage to conductor 90, as long as switch 26 remains in the ON position and the voltage level of battery 68 is sustained. The electric current flowing from the anode to the cathode of SCR 74 constitutes the signal which activates the audible alarm.

The values assigned to resistors 92 and 94 and capacitor 96 determine the time required to charge capacitor 96 to a voltage level at gate 98 sufficient to trigger SCR 74. A charging time of 0.5 seconds is attained with values of 1 megohm for both resistors 92 and 94 and 1 microfarad for capacitor 96 to induce conduction through a 2N5060 type SCR device, which is incorporated in the alarm circuit described herein. Thus, a programmed delay of 0.5 seconds is introduced between the actuation of mercury switch 54 and the provision of the supply voltage to conductor 90 to energize the timer circuits which produce the audible alarm signal. The sequential application of DC power to the electrical components in the alarm circuit is shown on lines A and B of the timing diagram of FIG. 7.

Resistor 102 is interconnected between electrode 57 of mercury switch 54 and DISCHARGE input terminal 104 of timer 78 to provide a voltage of known value to the inputs of the internal comparator circuits of timer 78 prior to the application of the supply voltage to terminal 84 of such timer. Applying the battery voltage to the DISCHARGE terminal of timer 78 in this manner establishes the desired set of input conditions within the timer circuit to ensure that output 106 of timer 78 will remain in the logic 0 state during and immediately after the application of the supply voltage to terminal 84. Resistor 102 is assigned a value of 10 kilohms to accomplish this purpose.

After the supply voltage has been applied to terminal 84, timer 78 provides a 1.5 Hz square wave at its output terminal 106. The 1.5 Hz oscillation frequency is established by assigning a value of 10 kilohms to timing resistor 108 and a value of 47 microfarads to timing capacitor 110. $\overline{\text{RESET}}$ terminal 112 of timer 78 is connected to conductor 90 to permit timer 78 to operate in a free-running astable mode as soon as the supply voltage is applied to the device. As shown on line C of FIG. 7, the 1.5 Hz square wave signal present at output terminal 106 remains at a logic 0 state during the first half-cycle following application of the supply voltage to terminal 84. Setting output 106 to a logic 0 state upon application of the supply voltage to terminal 84 of timer 78 averts the possibility of introducing an additional 0.33 second delay before sounding the alarm. Resistor 114 is assigned a value of 100 kilohms and is included to prevent an electrical imbalance within timer 78 which might cause destruction of the device during the time when voltage is applied to terminal 104, but not to supply voltage terminal 84.

Output terminal 106 of timer 78 is connected through resistor 116 to the base electrode of switching transistor 118, which is included to provide a logic inversion between output 106 of timer 78 and $\overline{\text{RESET}}$ input 120 of timer 80. Resistor 112 is disposed between conductor 90 and the collector electrode of transistor 118 to enable the electrical switching operation whenever a DC voltage is present on conductor 90. Resistors 116 and 122 are assigned values of 100 kilohms to bias transistor 118 in the switching mode. Transistor 118 can be a 2N2222A or any other small signal transistor device.

Timer 80 provides a 7.5 Hz square wave at its output terminal 124. The 7.5 Hz oscillation frequency is established by assigning the value of 100 kilohms to timing resistor 126 and a value of 1 microfarad to timing capacitor 128. Unlike timer 78, timer 80 is not a free-running oscillator because its output is controlled by transistor switch 118, the collector of which is connected direct to $\overline{\text{RESET}}$ input 120. Thus, whenever transistor switch 118 is conducting, its collector voltage corresponds to the logic 0 state. $\overline{\text{RESET}}$ input 120 will also be in the logic 0 state which will inhibit the oscillations of timer 80 and hold output 124 of timer 80 at logic 0. The effect of this arrangement, therefore, is that timer 80 operates as a gated oscillator which produces bursts of square wave output pulses at a 7.5 Hz rate in accordance with the logic state at its $\overline{\text{RESET}}$ input 120.

As a result of the logic inversion function performed by transistor 118, pulses are produced at output 124 of timer 80 whenever output 106 of timer 78 is in the logic 0 state. This generates a burst of five such pulses every 0.67 seconds. The timing relationship between the waveform present at output 106 of timer 78 and at output 124 of timer 80 is shown on lines C and D of FIG. 7. Resistor 130 is assigned a value of 10 kilohms and is disposed between conductor 90 and DISCHARGE terminal 132 of timer 80 to provide an external pull-up resistor for the integrated circuit timing device.

Timer 82 provides at its output terminal 134 a square wave with an adjustable nominal frequency of between 2-4 kHz. The range of oscillation frequencies is established by assigning a value of 500 kilohms to timing potentiometer 136, which is adapted to operate as a rheostat, and a value of 0.001 microfarad to timing capacitor 138. Output 124 of timer 80 is connected direct to $\overline{\text{RESET}}$ input 140 of timer 82 and thereby controls the presence of oscillations at output 134 of timer 82. Thus, timer 82 becomes a tone burst generator which produces a square wave output gated in accordance with the waveform at output 124 of timer 80 and has an oscillation frequency selectable within a 2–4 kHz range by means of varying the resistance of potentiometer 136.

As shown by way of example in lines D and E of FIG. 7, a series of 2 kHz pulses having a pulse cycle period of 0.5 msec is produced at output 134 of timer 82 whenever $\overline{\text{RESET}}$ input 140 is in the logic 1 state. Since the frequency of each tone burst is relatively substantially higher than the 7.5 Hz gating signal, the periods of sound emission are shown as cross-hatched pulses on line E of FIG. 7. A portion of one such tone burst of line E is magnified to show the structure of the audio signal waveform.

The audio frequency tone bursts of output 134 are applied to the base electrode of switching transistor 142 through resistor 144 which is assigned a value of 1 kilohm to establish the requisite base current to accomplish the switching operation. Transistor 142 may be the same type of device as that used for transistor 118.

An audio transducer 28, such as a Series QMB-01 device manufactured by Star Micronics, Inc., of New York, N.Y., is disposed between conductor 70 and the collector of transistor 142 to produce an audible signal in accordance with the tone burst pattern synthesized by the interconnection of timers 78, 80, and 82. The sound produced is syncopated in accordance with the change in logic states depicted on line D of FIG. 7. Such syncopation is desirable to produce a distinctive signal in a hospital setting where other audible paging signals are used for different purposes.

Diode 76 is disposed between the leads of audio transducer 28 to prevent the forward biasing of the collector-base junction of transistor 142 caused by negative-going voltage excursions produced in the inductive load of audio transducer 28 during the switching transitions of the tone bursts. Diode 76 may be an IN914 or similar device. Resistor 146 is assigned a value of 10 kilohms and serves the same function as an external pull-up as that of resistor 130.

Once it is activated, the alarm circuit will continue to emit an audible signal until the contacts of switch 26 are opened. This is true even though the patient may return to a position which would not have initially activated the alarm. This operational feature of the alarm circuit is due to the function of SCR 74 which will continue to conduct electric current, even though the trigger voltage has been removed from gate 98, and thereby provide the supply voltage to electrical conductor 90 as long as the voltage of battery 68 continues to be applied to anode 72.

The alarm circuit operates in a similar fashion whenever pressure switch 30 is closed, with the exception that the 0.5 second initial delay generating subcircuit is bypassed to sound the alarm immediately. Upon proper replacement of the monitoring system on the patient's thigh, the circuit will immediately cease producing an alarm signal. Opening the contacts of ON-OFF switch 26, therefore, is not required to deactivate the alarm in this instance.

It will be understood that upon substitution of an electromagnetic wave energy transmitter for audio transducer 28, the circuit described hereinabove can be used to produce an inaudible warning signal which can be received at a remote location.

Having illustrated and described what is presently the preferred embodiment of our invention, it should be apparent to those skilled in the art that this embodiment may be modified in arrangement and detail without departing from the principles of the invention which are intended to be illustrated but not limited by the disclosure. We therefore claim as our invention all such modifications as come within the true spirit and scope of the following claims.

What is claimed is:

1. An apparatus for monitoring the activity of a patient, comprising:
   switch means actuable in response to an amount of gravitational force corresponding to a preselected amount of downwardly directed inclination of the switch means;
   means to position the switch means on the patient's leg so that the switch means is actuated whenever the downwardly directed inclination of the femur portion of the leg proximal the knee exceeds the preselected amount;
   alarm means responsive to the actuation of the switch means to indicate that the patient is in an ambulatory enabling position; and
   means to detect an unauthorized removal of the switch means from the patient's leg.

2. The apparatus of claim 1 wherein the means to detect an unauthorized removal of the switch means includes a pressure-sensitive switch which is actuated in response to a substantial change in contact pressure between the patient's leg and the means to position the switch means thereon.

3. An apparatus for monitoring the activity of a patient, comprising:
   angle inclination sensing means to sense angular displacement relative to a predetermined datum plane, the sensing means being secured to and positioned on the femur portion of the patient's leg and including a mercury switch mounted on a carrier having a surface that contacts the patient's leg, the switch having two spaced-apart electrodes in the interior thereof and being inclined at a first angle relative to the carrier-contacting surface of the patient's leg so that the mercury in the switch makes simultaneous contact with the electrodes whenever the distal end of the femur portion is downwardly inclined relative to a horizontal datum plane at an angle that substantially equals the first angle;
   threshold detecting means operatively connected to the sensing means, the detecting means being responsive to produce a signal whenever the distal end of the femur portion assumes a downwardly directed angular inclination substantially equal to the first angle; and
   warning means in communication with the detecting means and actuated in response to the signal to provide notice that the patient is in an ambulatory enabling position.

4. The apparatus of claim 3 wherein the two electrodes of the mercury switch extend outwardly from the exterior thereof to determine the first angle.

5. The apparatus of claim 4 in which the electrodes extend from a portion of the mercury switch, which portion is positioned near the distal end of the femur.

* * * * *

UNITED STATES PATENT AND TRADEMARK OFFICE
CERTIFICATE OF CORRECTION

PATENT NO. : 4,536,755

DATED : August 20, 1985

INVENTOR(S) : Curtis R. Holzgang, Mark K. Leavitt, Alfred D. Doney and James Kuehn It is certified that error appears in the above-identified patent and that said Letters Patent are hereby corrected as shown below:

Column 8, line 22, after "logic" insert --state--; and

Column 8, line 24, "112" should be --122--.

Signed and Sealed this

Nineteenth Day of November 1985

[SEAL]

Attest:

Attesting Officer

DONALD J. QUIGG

Commissioner of Patents and Trademarks